(12) United States Patent
Wenger et al.

(10) Patent No.: US 10,436,707 B2
(45) Date of Patent: Oct. 8, 2019

(54) DETECTION OF ANALYTES USING NANOPARTICLES AS LIGHT SCATTERING ENHANCERS

(71) Applicants: Centre National de la Recherche Scientifique—CNRS, Paris (FR); Université d'Aix-Marseille, Marseilles (FR)

(72) Inventors: Jérôme Charles Wenger, Vitrolles (FR); Hervé Rigneault, Allauch (FR)

(73) Assignees: CENTRE NATIONAL DE LA RECHERCHE SCIENTIFIQUE—CNRS, Paris (FR); Université d'Aix-Marseille, Marseilles (FR)

( * ) Notice: Subject to any disclaimer, the term of this patent is extended or adjusted under 35 U.S.C. 154(b) by 0 days.

(21) Appl. No.: 15/513,260

(22) PCT Filed: Sep. 24, 2015

(86) PCT No.: PCT/EP2015/072022
§ 371 (c)(1),
(2) Date: Mar. 22, 2017

(87) PCT Pub. No.: WO2016/046335
PCT Pub. Date: Mar. 31, 2016

(65) Prior Publication Data
US 2017/0241901 A1 Aug. 24, 2017

(30) Foreign Application Priority Data
Sep. 25, 2014 (EP) .................................... 14306480

(51) Int. Cl.
| | |
|---|---|
| *G01N 21/00* | (2006.01) |
| *C12Q 1/68* | (2018.01) |
| *A61K 39/395* | (2006.01) |
| *C07H 21/00* | (2006.01) |
| *G01N 21/27* | (2006.01) |
| *G01N 21/51* | (2006.01) |
| *G01N 33/543* | (2006.01) |
| *G01N 21/47* | (2006.01) |
| *G01N 21/75* | (2006.01) |

(52) U.S. Cl.
CPC ........... *G01N 21/272* (2013.01); *G01N 21/51* (2013.01); *G01N 33/54346* (2013.01); *G01N 2021/4769* (2013.01); *G01N 2021/751* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 6,539,156 B1* | 3/2003 | Dickson | ................. | B82Y 20/00 385/129 |
| 8,137,920 B2* | 3/2012 | Chiang | ................ | G01N 33/587 435/7.1 |
| 2003/0207296 A1* | 11/2003 | Park | ...................... | C12Q 1/6816 435/6.11 |
| 2003/0211488 A1* | 11/2003 | Mirkin | ................. | C12Q 1/6816 435/6.12 |
| 2005/0175540 A1* | 8/2005 | Oraevsky | ............. | A61B 5/0095 424/9.5 |
| 2006/0024815 A1* | 2/2006 | Allman | ................ | G01N 21/253 435/287.2 |
| 2009/0170070 A1* | 7/2009 | Neerken | .......... | G01N 33/54306 435/5 |
| 2010/0285989 A1 | 11/2010 | Huo et al. | | |

FOREIGN PATENT DOCUMENTS

| | | |
|---|---|---|
| EP | 2 261 639 A1 | 12/2010 |
| JP | 2005-524849 A | 8/2005 |
| JP | 2010-185738 A | 8/2010 |
| JP | 4584352 B1 | 11/2010 |
| JP | 2013-533485 A | 8/2013 |
| WO | 03/095973 A2 | 11/2003 |
| WO | 2009/117168 A2 | 9/2009 |
| WO | 2012/006407 A2 | 1/2012 |

OTHER PUBLICATIONS

Elghanian et al. Science 277: 1078 (Year: 1997).*
Jans et al. Dynamic Light Scattering as a Powerful Tool for Gold Nanoparticle Bioconjugation and Biomolecular Binding Studies. Analytical Chemistry 81 (22) :9425 (Year: 2009).*
Written Opinion of the International Searching Authority issued in corresponding application No. PCT/EP2015/072022 dated Nov. 16, 2015 (8 pages).

(Continued)

Primary Examiner — Ethan C Whisenant
(74) Attorney, Agent, or Firm — Osha Liang LLP (57) ABSTRACT

A method for detecting the presence of an analyte (1) in a solution (2) comprising: providing at least a first and a second probes (A, B) different from each other, each probe (A,B) comprising a nanoparticle conjugated with a receptor specific to the analyte (1); contacting the solution (2) suspected of including the analyte (1) with the first and the second probes (A, B) to form a sample solution (3), wherein the sample solution (3) comprises aggregates (4) comprising the analyte (1) combined with the first and the second probes (A, B); illuminating the sample solution (3) with a light source having at least a first and a second exciting wavelengths ($\lambda_{eA}$, $\lambda_{eB}$) different from each other wherein the first and the second wavelength are chosen to get specific optical responses from the first probe (A) and the second probe (B) respectively when illuminated; detecting as a function of time the light scattered by the first probe (A) at a first detection wavelength ($\lambda_{dA}$) and the light scattered by the second probe (B) at a second detection wavelength ($\lambda_{dB}$) to get a first signal and a second signal respectively; and detecting temporal coincidences between said first signal and second signal.

12 Claims, 5 Drawing Sheets

(56) References Cited

OTHER PUBLICATIONS

International Search Report issued in corresponding application No. PCT/EP2015/072022 dated Nov. 16, 2015 (3 pages).
Rongchao Jin et al., "What Controls the Melting Properties of DNA-Linked Gold Nanoparticle Assemblies?"; Journal of the American Chemical Society, vol. 125, pp. 1643-1654; XP-002294467; Jan. 15, 2003 (12 pages).
Hilde Jans et al., "Dynamic Light Scattering as a Powerful Tool for Gold Nanoparticle Bioconjugation and Biomolecular Binding Studies"; Analytical Chemistry, vol. 81, No. 22, pp. 9425-9432; XP-055067927; Nov. 15, 2009 (8 pages).
Office Action issued in corresponding Application No. JP 2017-516762 dated Jun. 4, 2019 (9 pages).
Wenger, J. et al.; "Dual-color fluorescence cross-correlation spectroscopy in a single nanoaperture: towards rapid multicomponent screening at high concentrations"; Optics Express, vol. 14, No. 12, Dec. 11, 2006, pp. 12206-12216 (12 pages).
Wenger, J. et al.; "Biophotonics applications of nanometric apertures"; International Journal of Materials & Product Technology, vol. 34, No. 4, 2009, pp. 488-506 (20 pages).

* cited by examiner

DETECTION OF ANALYTES USING NANOPARTICLES AS LIGHT SCATTERING ENHANCERS

TECHNICAL FIELD

The present disclosure relates to a method and a system for detecting the presence of analytes, e.g., proteins, nucleic acids, DNA, bacterial fragments or other compounds in solution, the method using nanoparticles as light scattering enhancers.

BACKGROUND

Detection of analytes e.g., proteins, nucleic acids, DNA, bacterial fragments or other compounds, is important for both molecular biology research and medical applications. For example, detection of analytes allows determining the effect of an experimental treatment or the effect of a DNA mutation over all the biomolecules in a sample.

Several detection methods of analytes are available.

Enzyme-linked immunosorbent assay (ELISA) is used to detect the presence of a substance, usually an antigen, in a liquid sample or wet sample. It involves immobilizing an antigen to a solid surface and complexing the antigen with an antibody that is linked to an enzyme. Detection is accomplished by assessing the conjugated enzyme activity via incubation with a substrate to produce a measurable product. The reading of the measurable product is usually performed by chemiluminescence whose optical emission is weak.

Other techniques based on the detection of fluorescent molecules are widely used. These techniques comprise grafting a fluorescent molecule to the target analyte and analyzing the fluorescent emission. However, this approach requires many steps to isolate the grafted molecule of interest, and is limited by the weakness of the fluorescence signal and the photo degradation of the graft.

To avoid these issues, Gold Nano Particles (GNP) have attracted attention for bioassay development. GNPs can be prepared in a broad range of diameters (2 to 250 nm) with a high degree of precision and accuracy. Once prepared, they are stable for long periods, and because they are generally employed at very low concentrations they are economic to use even though the material from which they are made is relatively expensive. They are easily functionalized with recognition molecules (antibodies, antigens, oligonucleotides, etc.), thereby leading to highly stable conjugates. Assays using GNPs are mostly based on their optical and catalytic properties of GNPs. Metal nanoparticles have unique optical properties arising from their ability to support a localized surface plasmon resonance. More precisely, the localized surface plasmon resonance is the collective oscillation of the nanostructure conduction band electrons in resonance with the incident electromagnetic field. The spectrum of the localized surface plasmon resonance is strongly reliant upon the nanostructure size, shape and composition and the dielectric constant of the surrounding environment. As a result, a solution of nanoparticles has a characteristic color which can change depending on changes in the nanoparticles themselves and/or in the arrangement of the nanoparticles. It is these unique properties which have led to the development of metal nanoparticle based sensor technologies.

For example, a selective colorimetric detection method using GNP probes was developed by Elghanian et al (see "Selective Colorimetric Detection of Polynucleotides based on the distance-dependent Optical Properties of Gold Nanoparticles" Science Vol. 277 (1997)). Hybridization of the probe comprising GNPs with the target forms aggregates, causing a color visual change of the gold colloid solution from red (absence of hybridization) to purple (hybridization).

In order to obtain information on the particle dynamics with accuracy and chemical specificity, Jans et al, in "Dynamic light scattering as a powerful tool for gold nanoparticle bioconjugation and biomolecular binding studies" Anal. Chem. 81, 9425-9432 (2009), reports a technique which couples the use of Gold Nano Particle (GNP) probe as a light-scattering enhancer and Dynamic Light Scattering (DLS) as a read out system. The basic principle of DLS is as follows: a sample is illuminated by a laser beam and scattered light fluctuations due to the Brownian motion of the particle are detected at a known scattering angle by a fast photon detector. DLS instruments that measure the scattered light fluctuation as function of time and at a fixed angle can determine the mean particle size in a limited size range.

WO2009117168 also relates to an analytical method for the detection of an analyte using metal nanoparticles as light-scattering enhancers and DLS as a read out system. In this technique, a metal nanoparticle is conjugated with a plurality of identical or different receptors to form probes; a sample solution is formed by mixing the solution expected to include the analytes and the probes. In case of the presence of analytes, said analytes will bind to the receptors of the probes. To detect the presence of analytes, a light is directed towards the sample solution and the fluctuation over time of the light scattered by the sample solution is measured. From this measurement, DLS is used to quantify the amount of analyte by measuring the degree of aggregation in the solution. Aggregates comprising the analytes are distinguished from isolated probes in analyzing the nature of the DLS signal. However, this method shows a low signal to noise ratio which results in a limited sensitivity and a low specificity.

By sensitivity, it is meant the capacity to detect a minimum number of analytes per unit of volume. By specificity, it is meant the capacity to distinguish a specific analyte with a maximum of confidence.

The present invention proposes an original method and system for detecting the presence of an analyte, using nanoparticles as light scattering enhancers, which provides an excellent signal to noise ration and a very good specificity.

SUMMARY

An object of the present disclosure is to detect the presence of an analyte in a solution with accuracy and specificity, using a compact and low cost system.

According to a first aspect, the above-mentioned object, as well as further advantages, are achieved by a method for detecting the presence of an analyte in a solution comprising: providing at least a first and a second probes different from each other, each probe comprising a nanoparticle conjugated with a receptor specific to the analyte; contacting the solution suspected of including the analyte with the first and the second probes to form a sample solution wherein the sample solution comprises aggregates comprising the analyte combined with the first and the second probes; illuminating the sample solution with a light source having at least a first and a second exciting wavelengths $\lambda_{eA}$, $\lambda_{eB}$ different from each other, wherein the first and the second wavelength are chosen to get specific optical responses from the first probe and the second probe respectively when illuminated; detecting as a function of time the light scattered by the first probe at a first detection wavelength $\lambda_{dA}$ and the light scattered by the second probe at a second detection wavelength $\lambda_{dB}$ to get a first signal and a second signal respectively; and detecting temporal coincidences between said first signal and said second signal.

In the present disclosure, the optical response may be defined as a function giving, as a function of the detection wavelength, the ratio between the amount of light scattered by a nanoparticle in a given solid angle of detection at said detection wavelength and the amount of light incident on said nanoparticle. Practically speaking, the optical response may be obtained by illuminating the nanoparticles with a broad spectrum source ("white light") and measuring the scattered light as a function of the detecting wavelength. Since the nanoparticles are very small compared to the wavelength of the incident light, the scattering may be considered as isotropic and the optical response will present small variations when considering different solid angles of detection.

The method takes advantage of using two different probes bound to one analyte. As each probe has a specific optical response, the method enables to specifically detect the aggregate formed by the analyte combined with the at least first and second probes. When light scattered by the probes are detected simultaneously over time, it confirms the presence of the analyte in the solution. Through this method, a unique signature of a specific analyte is obtained with an excellent signal to noise ratio as the method enables to exclude the detection of signals originating from isolated probes.

Further, since the light scattered by the nanoparticles is intense, it is not necessary to use very sensitive detectors (e.g. avalanche photodiodes in Geiger mode or photomultiplier tubes) or microscope objectives with high aperture numbers; it results that a compact and low cost device may be used to implement the method according to the present description.

In some preferred embodiments, detecting the light scattered by the nanoparticle of the first probe and the nanoparticle of the second probe is made in a small observation volume, typically between 1 to 10 $\mu m^3$. For example, the observation volume may be limited by using a confocal microscopy arrangement. In limiting the observation volume, no more than one analyte will be present in the observed volume providing a contrasted detection signal and an increased accuracy of detection of the presence of the analyte.

In some embodiments, the light source has a broad spectrum allowing using one beam with the first and second wavelengths, thus making the system more compact.

Alternatively, the light source may comprise two independent light emitting devices for emitting a light beam ay each exciting wavelength, thereby allowing a better control of the illuminating step.

In some embodiments, detecting temporal coincidences between said first and second signals is achieved by detecting the scattered light in time windows having a predetermined width. The width of the time windows is adjusted according to the residence time (also referred to as the "diffusing time") of the GNPs-analyte aggregates in the observation volume. Typically, the residence time ranges between 1 to 50 ms, e.g. around 10 ms and the width of the time windows, corresponding to the temporal resolution of the detector, is set between a few microseconds and 1 ms.

Detection of temporal coincidences may be done in real time or via an a posteriori analysis of both signals.

In some other embodiments, detecting temporal coincidences between said first and second signals may be done using a correlator that provides cross correlation data between both signals. The correlator may work as an integrated microprocessor system.

According to a second aspect, there is proposed a system for detecting the presence of an analyte in a sample solution wherein the sample solution is suspected of including the analyte conjugated with at least a first and a second probes different from each other, each probe comprising a nanoparticle conjugated with a receptor specific to the analyte. The system comprises: a light source to illuminate the sample solution having at least a first and a second exciting wavelengths different from each other, wherein the first and the second wavelengths are chosen to get specific optical responses from the first probe and the second probe respectively when illuminated; a first optical system to collect the light scattered by the first probe and the second probe; at least one detector to detect as function of time the light scattered by the first probe at a first detection wavelength and the light scattered by the second probe at a second detection wavelength to get a first signal and a second signal respectively; a signal analysis system coupled to said detector(s) operable to detect temporal coincidences between said first signal and second signal.

The applicants have shown that the above described device may be particularly compact, the equivalent of a volume of 20 $cm^3$, as a high aperture objective or a high sensitivity sensor are not required.

In some other embodiments, the system may comprise a confocal pinhole to define an observation volume in which no more than one aggregate may be detected.

In some other embodiments, the signal analysis system may comprise a coincidence counter.

In some other embodiments, the signal analysis system may comprise a correlator.

In some other embodiments, the first optical system may also be used to focus the light emitted by the light source in the sample solution.

In some other embodiments, the system may comprise an optical fiber wherein an end part of the optical fiber (the distal part) is directed towards the sample solution and the other end part of the optical fiber (the proximal part) is optically connected to the light source and the at least one detector. This embodiment makes the system more practical and more flexible.

Other aspects and advantages of the present disclosure will be apparent from the following figures, description and appended claims.

BRIEF DESCRIPTION OF DRAWINGS

The present invention will be better understood and other advantages and embodiments will become clear on reading the following description, given by way of illustration only, and not limitation, this description referring to the appended figures in which.

DETAILED DESCRIPTION OF EMBODIMENTS

Embodiments of the present disclosure will now be described in detail with reference to the accompanying figures. It is intended that the following embodiments be considered as illustrative only, the scope of the invention not being limited to these embodiments. In the following detailed description of embodiments of the present disclosure, numerous specific details are set forth in order to provide a more thorough understanding of the present disclosure. However, it will be apparent to one of ordinary skilled in the art that the present disclosure may be practiced without these specific details. In other instances, well-known features have not been described in detail to avoid complicating the description unnecessarily.

Herein, the words "comprise/comprising" are synonymous with (means the same thing as) "include/including," "contain/containing", are inclusive or open-ended and do not exclude additional, unrecited elements. Further, herein the term "about" and "substantially" are synonymous with (means the same thing as) a 20% margin of the respective value.

Figure 1A:
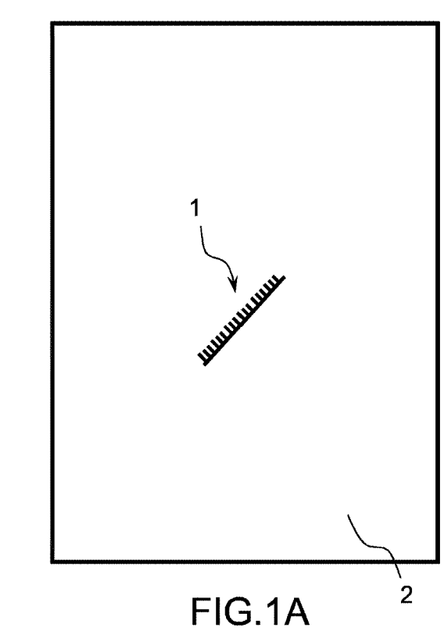
FIGS. 1A, 1B and 1C show different steps of the preparation of a sample solution for the detection of an analyte, according to the present description.
Figure 1B:
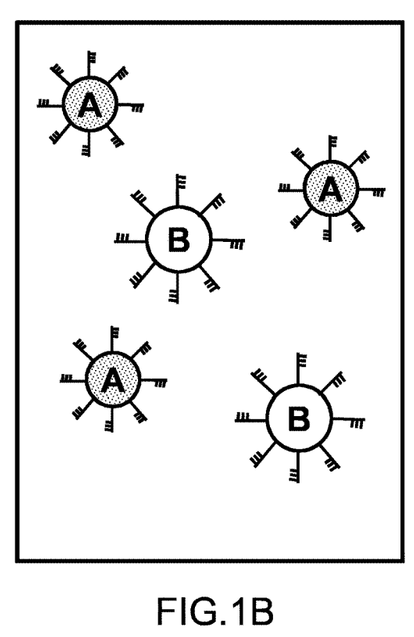
Figure 1C:
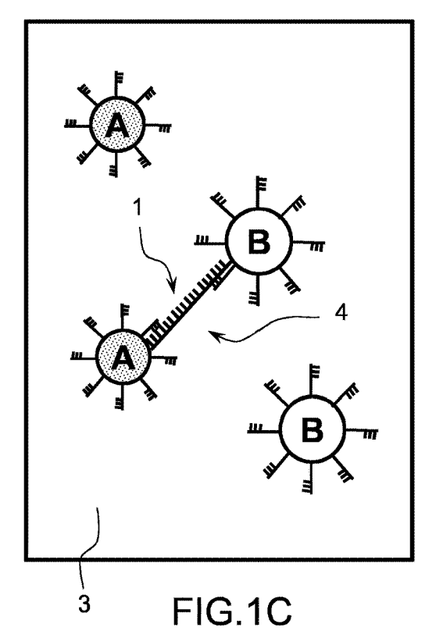

FIGS. 1A, 1B and 1C show different steps of the preparation of a sample solution for the detection of an analyte, according to the present description.

A solution 2 suspected of including the analytes 1 (FIG. 1A) is contacted with first and second probes A, B (FIG. 1B) to form a sample solution 3 (FIG. 1C).

The analytes 1 to be detected may comprise for example proteins (e.g.: an antigen), nucleic acids, DNA, bacterial fragments or other biological compounds. The solution 2 may comprise a liquid, a gaseous medium or a biological object that contains the analytes.

The first and second probes A, B are different from each other; each probe A and B comprises a specific nanoparticle conjugated with a receptor specific to the analyte 1. In other words, the first probe A comprises a first receptor and a first nanoparticle, while the second probe B comprises a second receptor and a second nanoparticle, wherein at least the second nanoparticle is different from the first nanoparticle.

The nanoparticles may be composed of a heart only or a heart and a shell which may comprise several layers. The nanoparticles may vary by the size, the shape, the composition and/or the material. The dimensions of the nanoparticles may be comprised between 20 and 200 nm. The shell or the heart may be dielectric or metallic and formed for example of silver, gold, silica or other metallic or dielectric materials. The nanoparticles may have for example a spherical or a rod shape. Some examples will be described below.

Each nanoparticle is bound to a receptor specific to the analyte to be detected. The receptor can be a natural receptor such as an antibody, a protein, a DNA, or a syntactic receptor such as molecules ions, polymers or other chemical species. The receptor of the probe A is complementary with a part of the analyte, while the receptor of the probe B is complementary with another part of the analyte. Each receptor may be conjugated to the corresponding nanoparticle with a chemical bond, e.g. a thiol group in the case of a nanoparticle made of gold.

As shown in FIG. 1C, when the probes A and B are put in contact with a solution 2 comprising the analyte 1, they combine with the analyte via a chemical bond created between the analyte 1 and each of the receptors to form an aggregate 4. The sample solution 3 to be tested thus comprises aggregates 4, and may also comprise isolated probes A and B and/or aggregates formed of an analyte combined with only one of the probes A or B (not shown in FIG. 1C). The method according to the present description aimed at selectively detecting aggregates formed of the analyte combined with both probes A and B, thus increasing the signal to noise ratio.

Although the method is described in the following using two different probes A and B, it may be advantageous, in some embodiments, to contact the solution 2 suspected to include the analyte 1 with more than two different probes, for example to detect analytes such as trimer. In this case, aggregates are formed with the analyte and the at least three different probes.

In some embodiments, the solution 2 may also comprise several different analytes intended to be detected simultaneously. In this case, the solution 2 may be contacted with different probes specific to each analyte, thus forming different aggregates that may be detected specifically, as it will be further detailed.

Figure 4A:
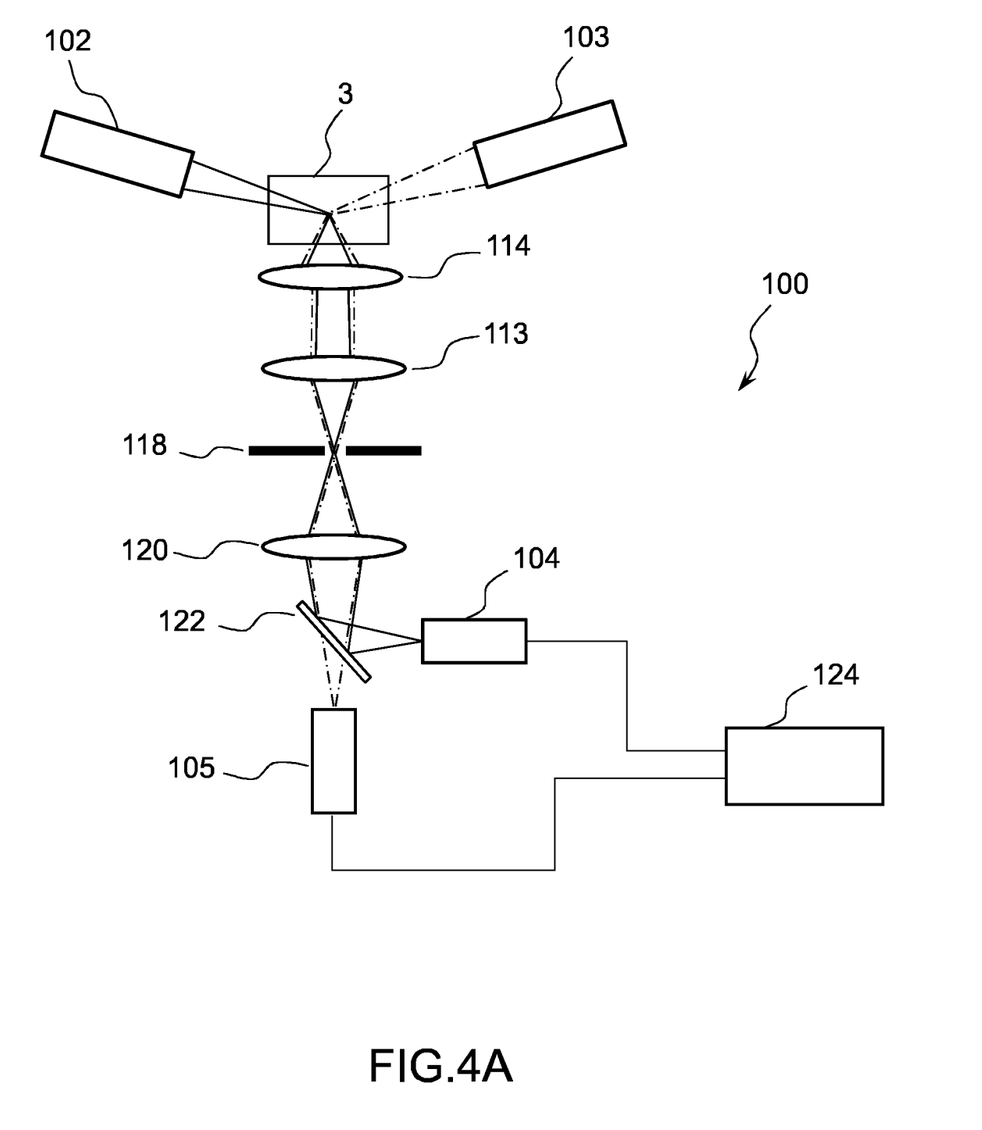
FIGS. 4A and 4B show two examples of systems for detecting the presence of an analyte according to examples of the present description.
Figure 4B:
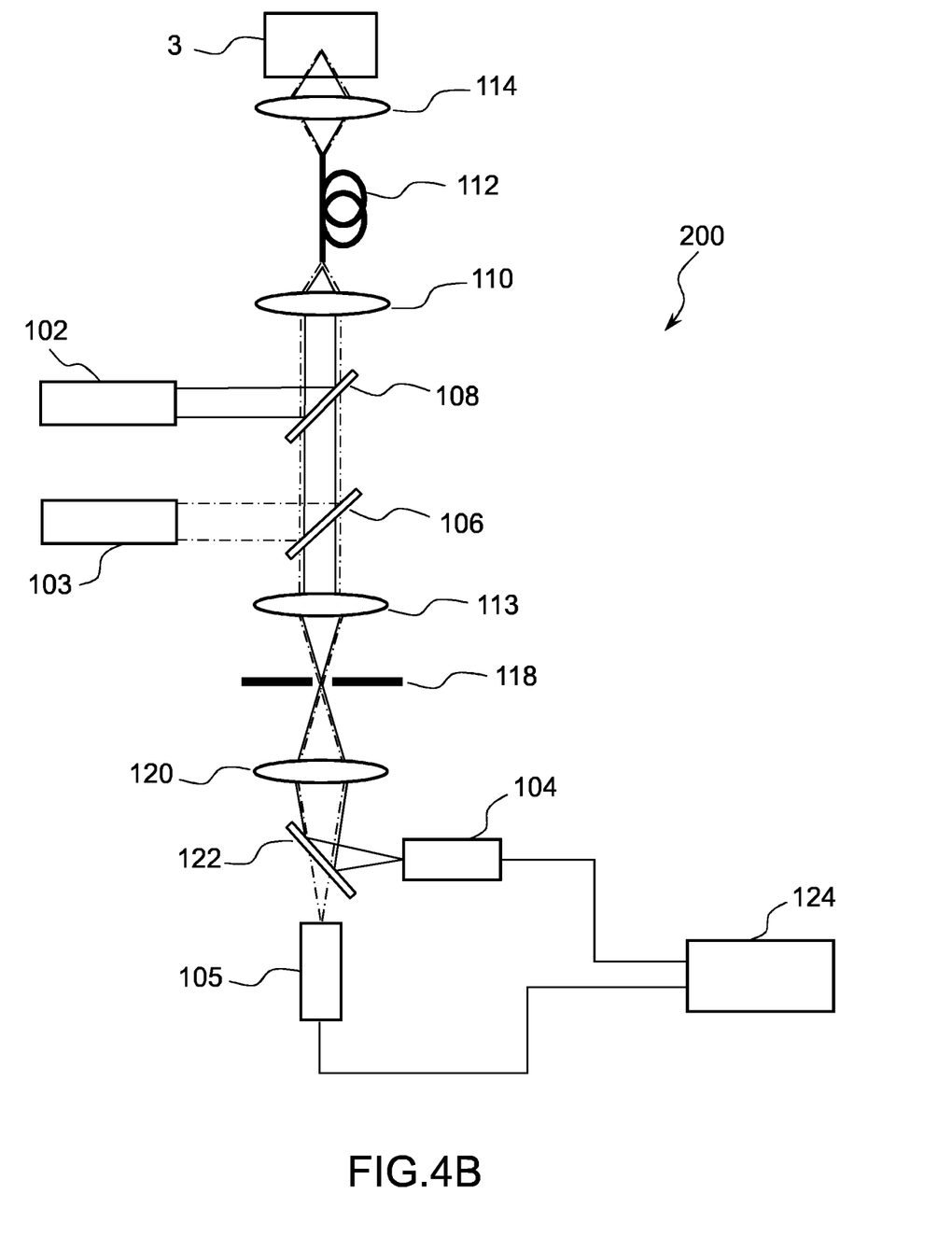

Once the solution 2 suspected to comprise the analyte to be detected is contacted with the different probes A and B, thus forming the sample solution 3, said sample solution is illuminated with a light source having at least a first and a second exciting wavelength ($\lambda e_A$, $\lambda e_B$) different from each other, and the light scattered by each of the probes A and B is detected and analyzed as described in greater details below, using a system as shown in FIGS. 4A and 4B.

According to embodiments of the present description, the system for detecting the presence of an analyte 1 in the sample solution 3 comprises, as shown in FIGS. 4A and 4B, a light source 102, 103 with two exciting wavelengths ($\lambda_{eA}$, $\lambda_{eB}$) different from each other, an optical system 114 (FIG. 4A, FIG. 4B) to collect light scattered by the nanoparticles, at least one detector (104, 105) to detect as function of time the light scattered by the first probe A and the second probe B and a signal analysis system 124 coupled to said detector(s) (104, 105) for analyzing the signals delivered by the detector(s).

Each exciting wavelength is advantageously chosen to maximize the optical response of one probe, while minimizing the optical response of the other probe.

In the present disclosure, the optical response may be defined as a curve giving as a function of the detection wavelength, the ratio between the amount of light scattered by a nanoparticle in a given solid angle of detection at said detection wavelength and the amount of light incident on said nanoparticle.

Figure 2:
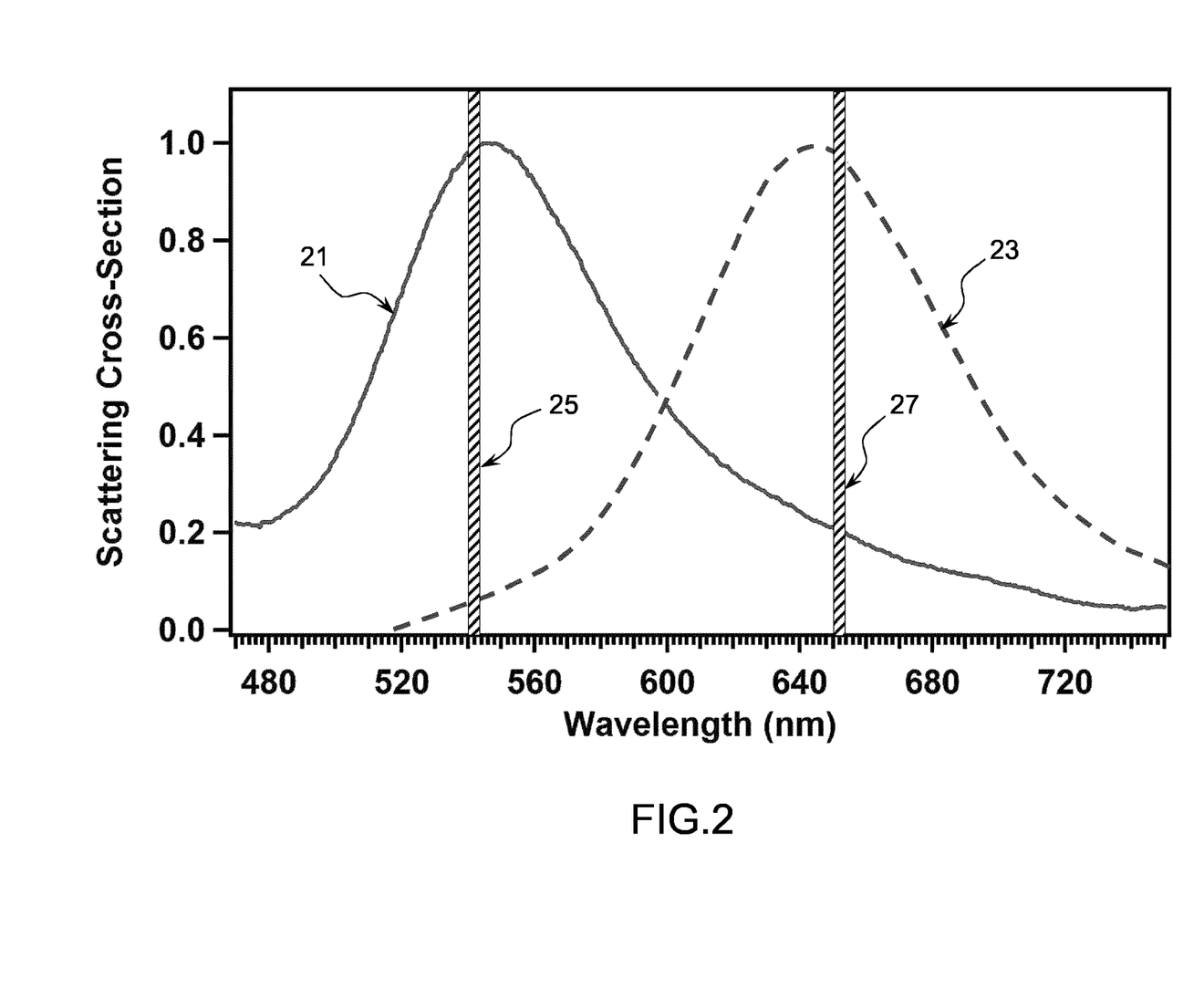
FIG. 2 shows examples of optical responses for two different probes adapted for the method according to the present description.

For purpose of illustration, FIG. 2 shows optical responses 21, 23 of two nanoparticles, respectively a first gold nanoparticle of 40 nm of diameter ("nanoparticle A") and a second gold nanoparticle of rod shape with a diameter of 25 nm and a length of 60 nm ("nanoparticle B"). A solution of water containing the nanoparticles A and B is illuminated with a collimated beam of white light from a halogen lamp whose propagation direction is set perpendicular to the detection collection path. Both spectra comprise a maximum at a specific central wavelength, respectfully 545 nm for the nanoparticle A and 640 nm for the nanoparticle B, which depends on the nature of the nanoparticle. Practically speaking, since the light scattered by a nanoparticle has a spectrum nearly similar than the spectrum of the illuminating light, detection may be performed at the exciting wavelength. When the spectra are well separated (in other words when the overlapping between the two spectra is minimized), it is thus possible to chose the exciting wavelengths that will maximize the optical response of one nanoparticle while minimizing the optical response of the other nanoparticle thus making the signature of a presence of a specific analyte more precise. As shown in FIG. 2, the exciting/detecting wavelengths may thus be slightly shifted from the central wavelengths.

As shown in FIGS. 4A and 4B, in some preferred embodiments, the light source may comprise two independent light emitting devices, e.g. a light emitting diode or a laser, each light emitting device emitting a light beam at the chosen exciting wavelength.

Alternatively, the light source may comprise a light emitting device with a broad spectrum including the two exciting wavelengths, such as a white light emitting device, e.g. an halogen lamp or a LED, with a spectrum between 400 and 800 nm. In this case, optical spectral filters may be used in the detection channels to limit the spectral bandwidth of the detected light.

The light source may be operated in continuous or in pulsed mode. If the light source operates in a pulsed mode, it may be necessary to choose a light source with a repetition time of the pulses relatively shorter than the residence time of the GNPs-analyte aggregates in the observation volume.

In some preferred embodiments, probes with metal nanoparticles are used, as the light scattered by metal nanoparticles, resulting from a localized surface plasmon resonance (see for example Mayer and Hainer, Chem. Rev. 2011, 111, 3828-3857), is strongly resonant with a specific exciting wavelength, which improves contrast and sensitivity of the detection.

Dielectric nanoparticles may also be used, in which case classical law of scattering effect is exploited. Dielectric nanoparticles may have the advantage to present a lower cost than metallic nanoparticles; however, the scattered light is usually less strong than the light scattered by metal nanoparticles.

The next step comprises the detection, as a function of time, of the light scattered by the first probe A at a first detection wavelength $\lambda_{dA}$ and the second probe B at a second detection wavelength $\lambda_{dB}$ present in the observation volume, so as to get a first and a second signal respectively.

The observation volume corresponds to the volume of the sample solution that can be detected by the system. It generally depends on the optical system 114 adapted to collect the scattered light and may be limited using, for example, a confocal arrangement as shown in FIGS. 4A and 4B.

In a confocal arrangement, out-of-focus light is eliminated by placing after the optical system 114 intended to collect the scattered light a field pinhole 118 (i.e., an aperture) in a plan conjugated with a region of interest of the sample. A lens 113 ensures with the optical system 114 the conjugation between the region of interest and the pinhole 118. The depth of field in the object space of the combined optical system 114, 113 together with the aperture of image of the pinhole in the object space of the combined optical system 114, 113 defines the observation volume. Signals from planes either above or below the observation volume are focused either above or below the conjugate image volume, which renders them inefficiently collected due to the location of the aperture through which the focused image is allowed to pass. Labeled analytes that are in the sample of interest are detected only when the aggregates are present in the confocal volume. In limiting the observation volume, no more than one analyte will be present in the observed volume providing a contrasted detection signal and thus, an increased accuracy for detection of the presence of the analyte.

In some preferred embodiments, two different detectors 104, 105 may be used, as shown in FIGS. 4A and 4B, each of the detector adapted to detect the light scattered by one of the probes. Said detectors may comprise a semiconductor photodiode, a photomultiplier module, an avalanche detector, a CMOS or a CCD sensor. A beam splitter 122, for example a dichroic mirror, is used to send the scattered light on each of the detectors.

Each detector is adapted for detecting the scattered light at a specific wavelength, for example a wavelength close to the exciting wavelength. In preferred embodiments, the detection spectral band has a limited width to specifically detect the scattered light from one nanoparticle and thus increase the signal to noise ratio. In some preferred embodiments, the spectral band width is smaller than 20 nm, preferentially smaller than 10 nm. The dichroic mirror 122 may be used to isolate the different detection spectral bands. Specific spectral filters may also be used in each detection channel.

In the example shown in FIG. 2, area 25 and 27 respectfully illustrate the detection "bandwidth" or "the spectral band used for detection" of the nanoparticles A (a gold nanoparticle of 40 nm of diameter) and the nanoparticles B (a gold nanoparticle of rod shape with a diameter of 25 nm and a length of 60 nm). In this example, the light scattered by the nanoparticle A is detected around 545 nm with a spectral band width of around 5 nm and the light scattered by the nanoparticle B is detected at about 650 nm with a spectral band width of about 5 nm.

The detection is made as a function of time over a time period sufficiently long, typically 1 s or more. The detector may acquire permanently the signal during the measurement or, alternatively, in a time-gated mode, by using for example a silicon photodiode. The temporal resolution of the detectors is preferably less than 1 ms which is considered to be much less than the residence time which is around 10 ms.

Figure 3:
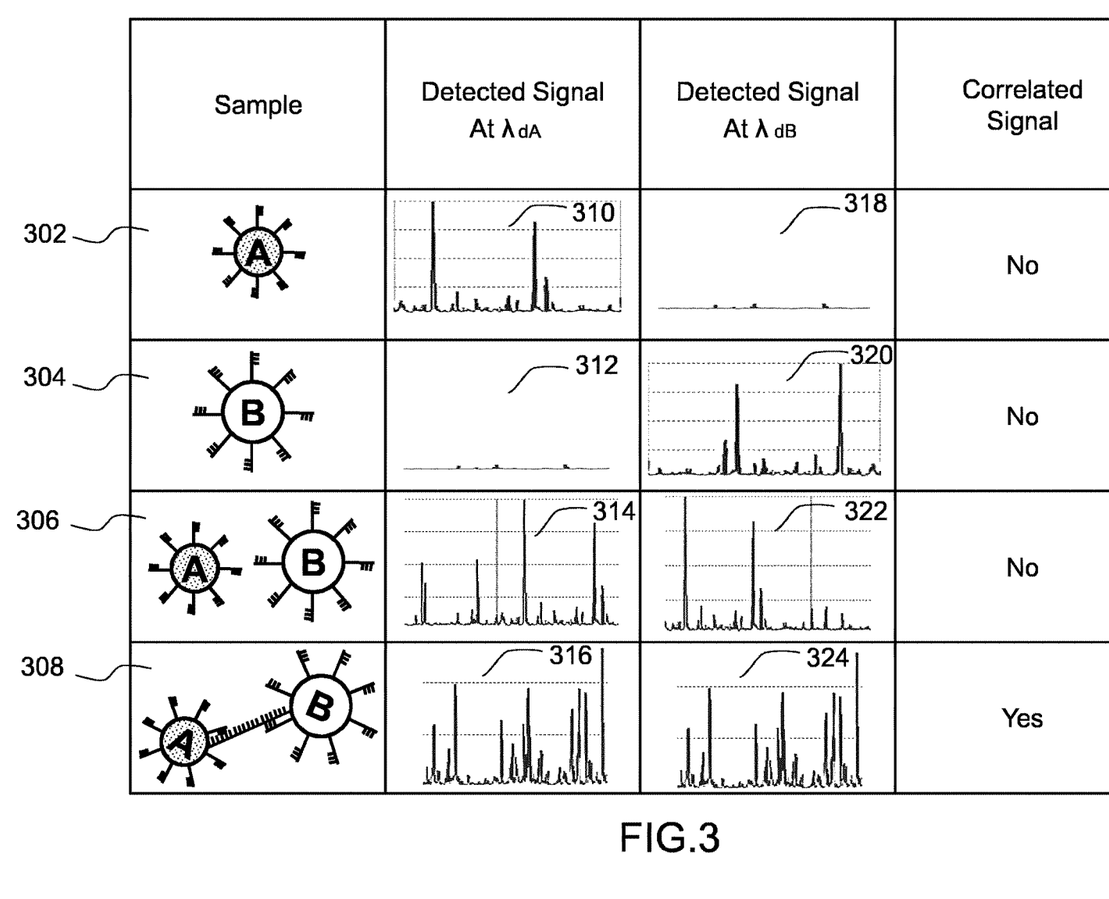
FIG. 3 is a table illustrating signal detections as a function of time for, respectively, a single probe A, a single probe B, probes A and B alone (i.e. not combined with an analyte) and probes A and B combined with an analyte, according to an example.

The table of FIG. 3 shows the signals measured by each detector as a function of time and for different samples present in the observation volume.

In a first example, only one probe A is present in the observation volume (sample 302); in this first example, a signal 310 is observed on the detector 104 adapted to detect the scattered light at the detecting wavelength $\lambda_{dA}$ of the nanoparticle A, but no signal is observed on the detector 105 (see 318) as no nanoparticle B is present in the observation volume. In the second example, only one probe B in present in the observation volume (sample 304); in this second example, a signal 312 is observed on the detector 105 adapted to detect the scattered light at the detecting wavelength $\lambda_{dB}$ of the nanoparticle B, but no signal is observed on the detector 104 (see 320) as no nanoparticle A is present in the observation volume. When analyzing respectively the two signals 310 and 318 on the one hand, and 312 and 320 on the other hand, no significant number of temporal coincidences between the two signals would be monitored and consequently, no conclusion could be made of the analyte present in the observation volume. Note that the observed signals would be the same if each of the probes A and B in the first and second example respectively would be conjugated to one analyte. However, no conclusion would be made regarding the presence of the analyte.

In a third example, a probe A and a probe B are present in the observation volume (sample 306) but they are not conjugated with an analyte; consequently, a signal 314 is observed on the detector 104 and a signal 322 is observed on the detector 105. However, the signals are not correlated, in other words they fluctuate independently as function of time, since the nanoparticles A and B may move out of the observation volume independently from each other. When analyzing the two signals 314 and 322, no significant number of temporal coincidences between the two signals would be monitored and consequently, no conclusion could be made of the analyte present in the observation volume.

In a fourth example, both a probe A and a probe B are in the observation volume, and are conjugated with the same analyte (sample 308); a signal 316 is observed on the detector 104 and a signal 324 is observed on the detector 105. The signals are correlated, in other words they fluctuate in concert. There are a significant number of temporal coincidences between the two signals (i.e. superior to the noise occurrence of temporal coincidences) and conclusion can be made regarding the presence of the analyte.

The temporal coincidences detection is based on the analysis of the scattered light fluctuations due to the Brownian motion of the nanoparticles. Measuring the scattered fluctuations may also be made by computing temporal cross-correlations using a correlator. Cross correlation extends standard auto correlation by introducing two different probes with distinct excitation and emission properties that can be detected in the same confocal volume. It temporally correlates the intensity fluctuations of two distinguishable probes. Coincidence of these signal probes on the same analyte is detected as a change in amplitude F, at a delay time T. The general expression for fluctuations cross-correlation functions is given by:

$$G_{AB}(\tau) = \frac{<F_A(t)^* F_B(t+\tau)>}{<F_A(t)> <F_B(t+\tau)>}$$

where $F_A(t)$, $F_B(t)$ are the scattered photo count signals for probes A, B and <.> stands for time averaging.

Thus for cross-correlation, there is perfect correlation when the fluctuations in the two signals are caused by the same source. If the two signals fluctuate independently, correlation between them is zero at all times. In cross-correlation mode, only pairs of coincident photon counts from two distinct channels will be recorded as a positive result.

In some embodiments of the present application, the temporal coincidences may be performed with a coincidence counter which allows recording detection signals that strike detector(s) simultaneously.

In some embodiments of the present application, the temporal coincidences may be performed combining the cross correlation and the coincidence counter.

In some embodiments of the present application, the method of the present invention may comprise a calibration step. The calibration step comprises detecting the scattered light at the first and second detection wavelength using a calibration solution which only contains probes A and B but no analyte. It is thus possible to estimate the noise of the detection by evaluating the number of time coincidences between the two signals (noise threshold). In this way, a number of time coincidences may be considered as significant when it is superior than the noise threshold as estimated.

As explained through the description of FIG. 3 above, the method takes advantage of using two different probes conjugated with one analyte. As each probe has a specific optical response, when the two specific optical responses are detected simultaneously, it confirms the presence of the analyte in the solution. This method allows a unique signature of a presence of a specific analyte to be obtained.

From the data generated by the method according to the present disclosure, a variety of information can be obtained including, for example, the presence of the analyte, the concentration, the size and the kinetics of the analytes in a solution as it is usually obtained from the DLS signals (see for example Jans et al in "Dynamic light scattering as a powerful tool for gold nanoparticles bio conjugation and bio molecular binding studies" Anal. Chem. 81, 9425-9432 (2009)).

While the above examples have been described using two separate detectors, it is also possible to use a single detector. In the case of a single detector, two independent light sources may be used. Thus the single detector may allow the detection on a broad spectrum and allow to be synchronized with each independent light source.

FIGS. 4A and 4B show different embodiments of devices 100, 200 for detecting the presence of an analyte according to the present description.

A device for detecting the presence of an analyte according to an example of the present description comprises a light source 102,103, a first optical system 114, detectors 104, 105 and a signal analysis system 124.

In the example of FIGS. 4A and 4B, the light source comprises two independent light emitting devices 102, 103 to illuminate the sample solution 3. The two independent light emitting devices emit light beams having respectively a first and a second exciting wavelength ($\lambda_{eA}$, $\lambda_{eB}$) different from each other and adapted to get specific optical responses from the probes A and B.

A first optical system 114, e.g. a lens, a plurality of lenses or a microscope objective is used to collect the light scattered by the nanoparticles in an observation volume, the scattered light forming a return light beam.

In one embodiment of the present invention, the device may comprise a second optical system to focus the light beams emitted by the light source(s) in the sample solution.

In one embodiment of the present invention as previously explained, as illustrated in FIG. 4B, the first and second optical systems are the same, the first optical system being also used to focus the light beam emitted by the light source in the sample solution. In this case, semi reflective mirrors may be used in order to allow the light beams emitted by the two independent light emitting devices to reach said first optical system.

In one embodiment of the present invention, the observation volume of the sample 3 may be further limited by using a confocal arrangement. As illustrated in FIGS. 4A and 4B, a confocal arrangement comprises a lens 113 and a pinhole 118 arranged at the focal point of the lens 113. The dimension of the pinhole 118 may be advantageously adjustable.

In one embodiment of the present invention, as illustrated in FIGS. 4A and 4B, a spectral separator 122 may be arranged in the optical way of the return light beam to separate the light scattered by the first probe (A) and the light scattered by the second probe (B) and to direct to the detectors. This separator may be a dichroic filter, arranged, for example at 45° with respect to the optical way of the return light beam.

The detectors 104 and 105 receive the light scattered respectively by the first and second probes A and B and are adapted to detect the scattered light at a first detection wavelength ($\lambda_{dA}$) and at a second detection wavelength ($\lambda_{dB}$) respectively.

The detectors may be coupled to a signal analysis system operable to detect temporal coincidences between said first and second signal. The signal analysis system 124 may comprise a coincidence counter and/or a correlator which make it possible to numerically process the received data. Particularly, the counter may record the detected scattered light intensity value at different time windows and the correlator may carry out the temporal analysis of the received light intensity fluctuations.

In one embodiment of the present invention, as illustrated in FIG. 4B, an optical fiber 112 may be arranged between the first optical system and the detection channel. An end part of the fiber 112 (the distal part) is directed towards the lens 114 and the sample solution. The other end of the fiber 112 (the proximal part) is optically connected to the light source and the at least one detector, to guide the light emitted by the light source towards the sample solution and to guide the light scattered by the sample solution towards the lens 110 and the detectors.

The skilled person may note that other means for the confocal arrangement may be used such as replacing the pinhole by a hole in a metallic plate or by an optical fiber, the core diameter of the optical fiber setting the useful aperture.

In one embodiment of the present invention, the solution 2 may comprise several different analytes intended to be detected simultaneously. In this case, the solution 2 may be contacted with different probes specific to each analyte, thus forming different aggregates that may be detected specifically. In this case, light scattered by each probe is detected at a specific detection wavelength. Temporal coincidences may then be detected between the two signals resulting from the light scattered by the probes conjugated to the same aggregate. Thus, it is possible to detect the presence of different analytes in the same sample solution simultaneously.

The above-mentioned systems offer many applications in the field of biological tests in liquid medium, particularly for scientific research, medical tests, food industry analysis, the chemical and pharmaceutical industry and defense.

The previously described embodiments of the present invention are given by way of examples and are in no way limitative. It is obvious that the skilled person is able to achieve different alternatives of the invention within the framework of the patent.

The invention claimed is:

1. A method for detecting presence of an analyte in a solution comprising:
providing at least a first probe and a second probe different from each other, each probe comprising a nanoparticle conjugated with a receptor specific to the analyte, the first probe and the second probe having spectral optical responses separated from each other, wherein the spectral optical response of each probe is defined as a function of wavelength by a ratio between light scattered by the probe in a given solid angle of detection at the wavelength and an amount of light incident on the probe, wherein the nanoparticle of the second probe is different from the nanoparticle of the first probe;
contacting the solution with the first probe and the second probe to form a sample solution, wherein the sample solution comprises aggregates comprising the analyte combined with the first probe and the second probe;
illuminating the sample solution with a light source having at least a first exciting wavelength and a second exciting wavelength different from each other wherein the first exciting wavelength and the second exciting wavelength are chosen to get distinct optical responses from the first probe and the second probe respectively when illuminated;
detecting as a function of time light scattered by the first probe at a first detection wavelength and light scattered by the second probe at a second detection wavelength different from the first detection wavelength to get a first signal and a second signal respectively;
detecting temporal coincidences between the first signal and the second signal; and
detecting the presence of the analyte based on the detection of temporal coincidences.

2. The method of claim 1, wherein detecting the light scattered by the first probe and the second probe is made in an observation volume limited by using a confocal microscopy arrangement.

3. The method of claim 1, wherein the nanoparticles are metal nanoparticles.

4. The method of claim 1, wherein the detecting of the light scattered by the first probe and the second probe comprises detecting back scattered light.

5. The method of claim 1, wherein detecting temporal coincidences between said first signal and said second signal comprises detecting the light scattered in time windows having a predetermined width.

6. The method of claim 1, wherein detecting temporal coincidences between said first signal and said second signal comprises using a correlator.

7. A system configured for detecting the presence of an analyte in a sample solution wherein the sample solution is formed when a solution suspected of including the analyte is conjugated with at least a first probe and a second probe different from each other, each probe comprising a nanoparticle conjugated with a receptor specific to the analyte, the system comprising:
a light source configured to illuminate the sample solution with a light beam having at least a first exciting wavelength and a second exciting wavelength different from each other wherein the first exciting wavelength and the second exciting wavelength are chosen to get distinct optical responses from the first probe and the second probe respectively when illuminated, wherein the nanoparticle of the second probe is different from the nanoparticle of the first probe;
a first optical system configured to collect light scattered by the first probe and the second probe, wherein said at least first probe and second probe have spectral optical responses separated from each other;
at least one detector configured to detect as a function of time light scattered by the first probe at a first detection wavelength and light scattered by the second probe at a second detection wavelength different from said first detection wavelength to get a first signal and a second signal respectively;
a signal analysis system coupled to said at least one detector and configured to detect temporal coincidences between said first signal and second signal and to detect the presence of the analyte based on said detection of temporal coincidences.

8. The system of claim 7, further comprising a confocal pinhole to define an observation volume in which no more than one aggregate may be detected.

9. The system of claim 7, wherein the signal analysis system comprises a coincidence counter.

10. The system of claim 7, wherein the signal analysis system comprises a correlator.

11. The system of claim 7, wherein the first optical system is further configured to focus the light emitted by the light source on the sample solution.

12. The system of claim 11, further comprising an optical fiber wherein a first end part of the optical fiber is directed towards the sample solution and a second end part of the optical fiber is optically connected to the light source and the at least one detector.

* * * * *